United States Patent
Levi et al.

(10) Patent No.: US 10,244,858 B2
(45) Date of Patent: Apr. 2, 2019

(54) VIBRATING BRUSH ASSEMBLY FOR PERSONAL HYGIENE DEVICE

(71) Applicant: BZL Medical Ltd., Habonim (IL)

(72) Inventors: BenZion Levi, Habonim (IL); Sefi Shachrur, Pardes-Hana Karkur (IL)

(73) Assignee: BZL Medical Ltd., Habonim (IL)

( * ) Notice: Subject to any disclaimer, the term of this patent is extended or adjusted under 35 U.S.C. 154(b) by 70 days.

(21) Appl. No.: 15/451,641

(22) Filed: Mar. 7, 2017

(65) Prior Publication Data
US 2018/0255916 A1    Sep. 13, 2018

(51) Int. Cl.
| | |
|---|---|
| A46B 13/02 | (2006.01) |
| A46B 15/00 | (2006.01) |
| A61C 17/34 | (2006.01) |
| A46B 9/04 | (2006.01) |

(52) U.S. Cl.
CPC .......... *A46B 13/023* (2013.01); *A46B 15/004* (2013.01); *A46B 15/0022* (2013.01); *A46B 15/0036* (2013.01); *A46B 9/04* (2013.01); *A61C 17/3481* (2013.01)

(58) Field of Classification Search
CPC ..... A46B 9/04; A46B 13/023; A46B 15/0022; A61C 17/3481
See application file for complete search history.

(56) References Cited

U.S. PATENT DOCUMENTS

| | | | | |
|---|---|---|---|---|
| 7,646,117 B2* | 1/2010 | Shimizu | ............. | A61C 17/3445 15/22.1 |
| 8,239,991 B2* | 8/2012 | Shimizu | ............. | A46B 15/0002 15/22.1 |
| 2002/0120991 A1* | 9/2002 | Cacka | .................. | A61C 17/225 15/22.1 |
| 2004/0261203 A1* | 12/2004 | Dworzan | ........... | A61C 17/3481 15/22.1 |
| 2008/0183249 A1* | 7/2008 | Kitagawa | ........... | A46B 15/0002 607/79 |
| 2015/0052696 A1* | 2/2015 | Simeth | ................... | A61C 17/16 15/22.1 |

\* cited by examiner

*Primary Examiner* — Randall Chin
(74) *Attorney, Agent, or Firm* — Dekel Patent Ltd.; David Klein

(57) ABSTRACT

A personal hygiene device includes a vibrator housed in a handle. A shaft is coupled to the vibrator and extends from the vibrator to a brush head. The shaft is electrically conducting and includes one or more proximal electrical contacts in electrical contact with an electrical source and one or more distal electrical contacts in electrical contact with one or more electrical elements located in the brush head. The shaft is configured to transfer vibrational energy created by the vibrator to the brush head to vibrate the brush head.

10 Claims, 4 Drawing Sheets

VIBRATING BRUSH ASSEMBLY FOR PERSONAL HYGIENE DEVICE

FIELD OF THE INVENTION

The present invention relates generally to personal hygiene devices, and particularly to a personal hygiene device with a brush head that has electrical elements and a vibrator shaft assembly that transfers both electrical energy and mechanical forces from the vibrator to the brush head.

BACKGROUND OF THE INVENTION

Personal hygiene cleaning devices that have a brush head include, for example, toothbrushes, skin care products and many others. There are other devices that include RF (radio-frequency) electrodes that apply RF energy to hair, skin or body tissues for various purposes, such as depilation, acne treatment, ablation and others.

SUMMARY OF THE INVENTION

The present invention seeks to provide a personal hygiene device with a brush head that has electrical elements and a vibrator shaft assembly that transfers both electrical energy and mechanical forces from the vibrator to the brush head, as is described more in detail hereinbelow.

In one embodiment, the device includes a vibrator, such as a vibrating motor. Instead of the shaft of the vibrator being a simple non-conducting shaft, the shaft is electrically conducting and includes multiple electrical contacts. The shaft extends from the vibrator to the brush head and transfers the vibrational energy created by the vibrator to the brush head to vibrate the brush head. The shaft also transfers electrical energy from an electrical source (e.g., battery, RF (radio frequency) generator) to electrical elements in the brush head, such as electrodes, RF electrodes, sensors, indicators, lights (e.g., LEDs), brush head connected indication or other electrical components. The shaft may be connected to the brush head with a snug fit, snap fit or other suitable connection.

There is thus provided in accordance with an embodiment of the present invention a personal hygiene device including a vibrator housed in a handle, and a shaft coupled to the vibrator that extends from the vibrator to a brush head, the shaft being electrically conducting and including one or more proximal electrical contacts in electrical contact with an electrical source and one or more distal electrical contacts in electrical contact with one or more electrical elements located in the brush head, and wherein the shaft is configured to transfer vibrational energy created by the vibrator to the brush head to vibrate the brush head.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
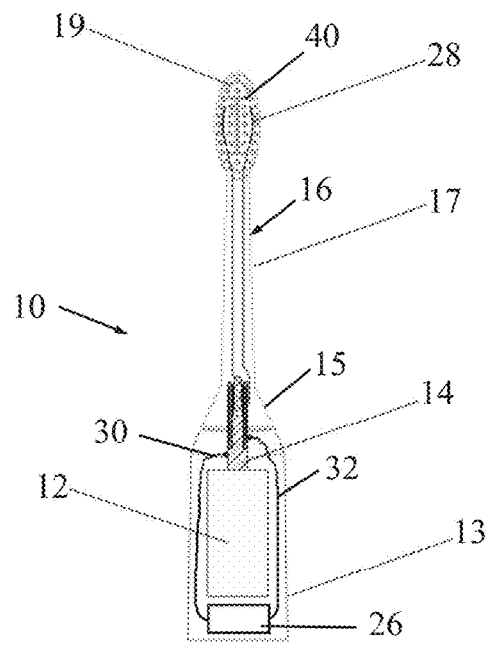
FIG. 1 is a simplified pictorial illustration of a personal hygiene device, in accordance with a non-limiting embodiment of the invention.

Reference is now made to FIGS. 1-4, which illustrate a personal hygiene device 10, constructed and operative in accordance with a non-limiting embodiment of the present invention.

Device 10 includes a vibrator 12, such as a vibrating motor, solenoid, linear vibrating motor and the like, housed in a hand piece 13. A shaft 14 is coupled to vibrator 12 and extends from vibrator 12 to a brush head 16. Shaft 14 may be assembled to brush head 16 with a snug fit, snap fit or other suitable connection. Shaft 14 transfers the vibrational energy created by vibrator 12 to brush head 16 to vibrate brush head 16. The brush head 16 may have a relatively wide base 15 and a relatively narrow body portion 17 that leads to bristles 19 at the distal end of brush head 16. Although the illustrated embodiment shows shaft 14 extending into base 15 and barely extending into body portion 17 (without limitation, about 1-30 mm), nevertheless shaft 14 may extend further into body potion 17 and even the full length of body portion 17 in other embodiments.

Shaft 14 is electrically conducting, and as such, is made of an electrically conducting material, such as but not limited to, stainless steel, copper or copper alloy, aluminum or aluminum alloy and the like. Shaft 14 may be rigid to transfer in one-to-one correspondence the vibrations or oscillations created by vibrator 12. Alternatively, shaft 14 may be flexible, in which case, shaft 14 either transfers in one-to-one correspondence the vibrations or oscillations created by vibrator 12 or amplifies or modifies the vibrations or oscillations in accordance to the natural frequency of the shaft 14 and its boundary conditions (e.g., cantilevered or supported at some point along its axial length).

Figure 2:
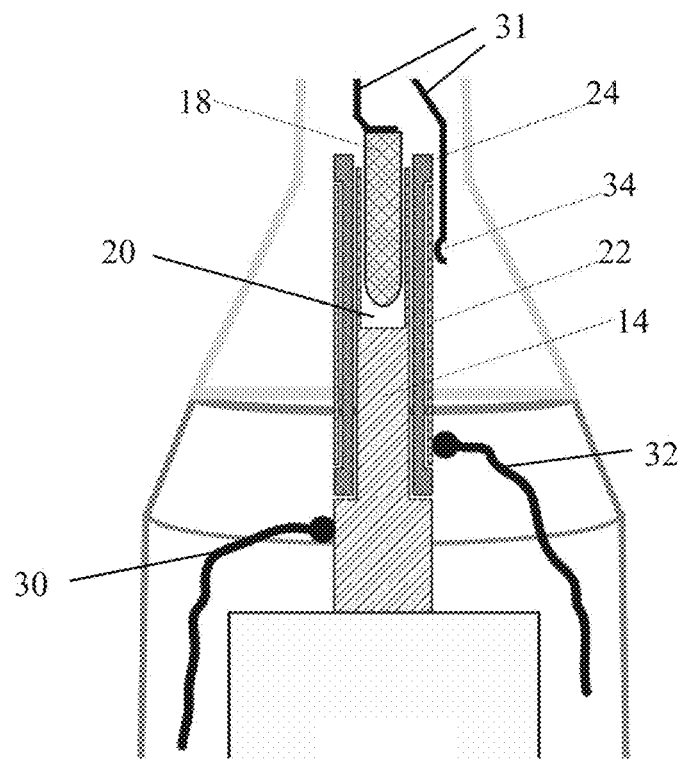
FIG. 2 is an enlarged illustration of a shaft that extends from a vibrator to a brush head in the personal hygiene device of FIG. 1, showing RF electrical connections.
Figure 3:
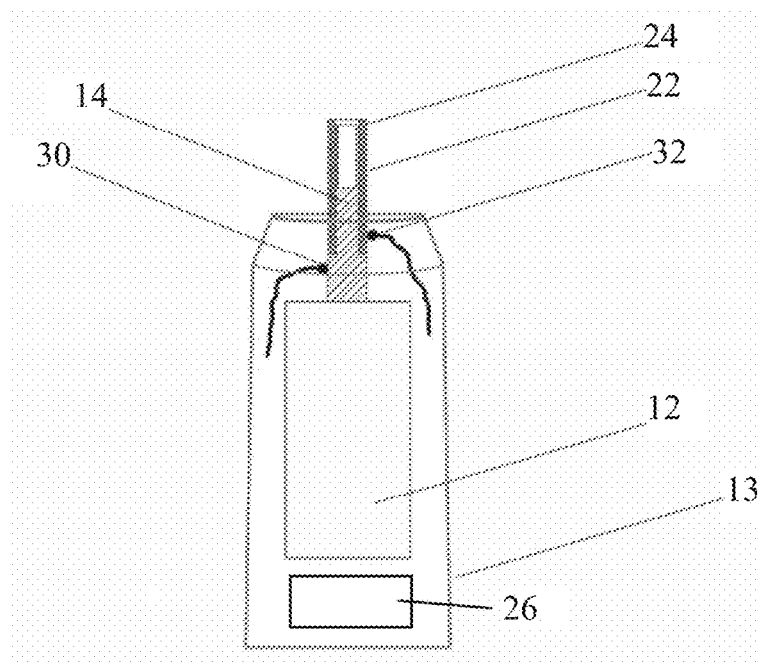
FIG. 3 is a simplified illustration of the hand piece, vibrator and shaft of the personal hygiene device of FIG. 1.
Figure 4:
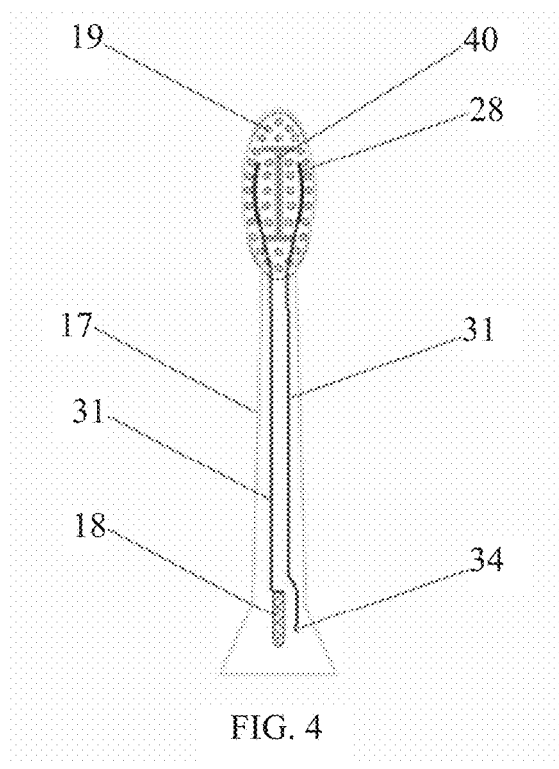
FIG. 4 is a simplified illustration of the brush head of the personal hygiene device of FIG. 1.
Figure 5:
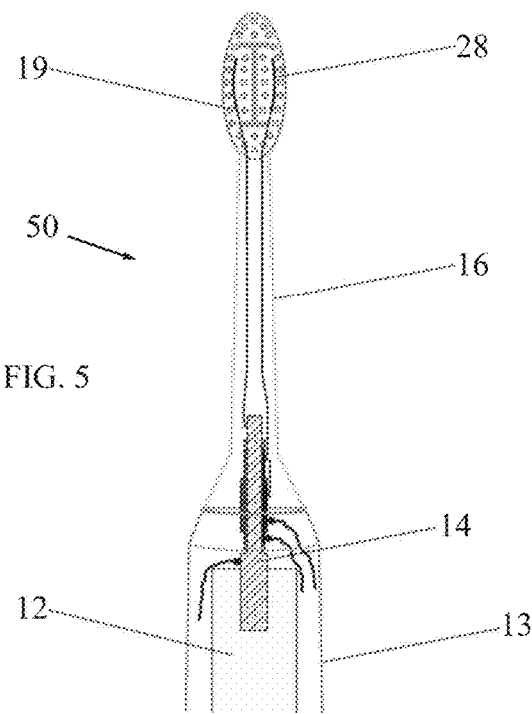
FIG. 5 is a simplified pictorial illustration of a personal hygiene device, in accordance with another non-limiting embodiment of the invention.
Figure 6:
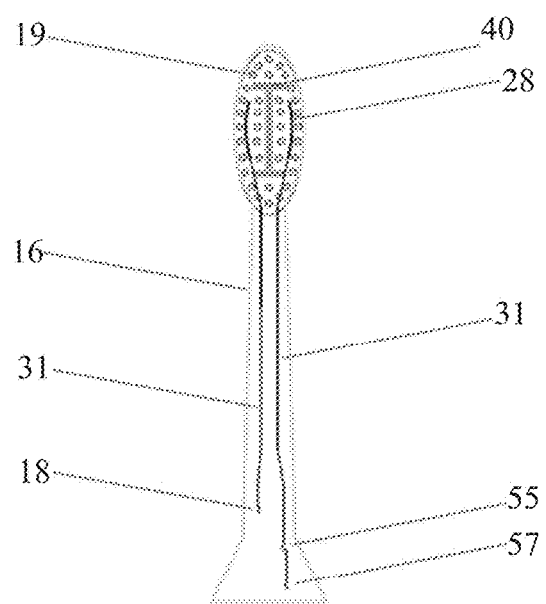
FIG. 6 is a simplified illustration of the brush head of the personal hygiene device of FIG. 5.
Figure 7:
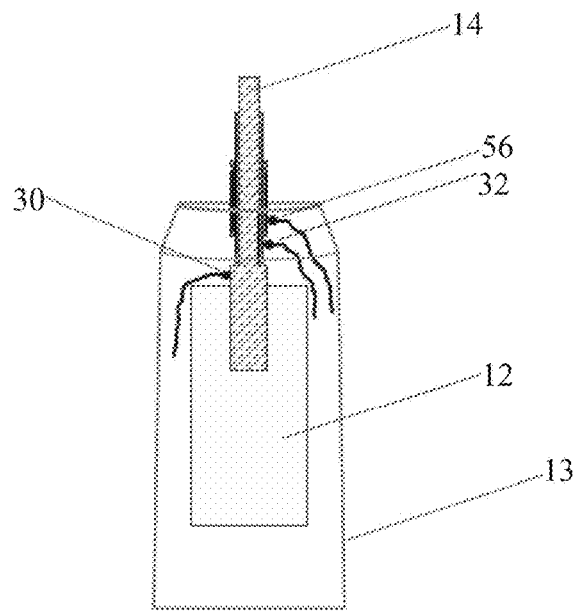
FIG. 7 is a simplified illustration of the hand piece, vibrator and shaft of the personal hygiene device of FIG. 5.
Figure 8:
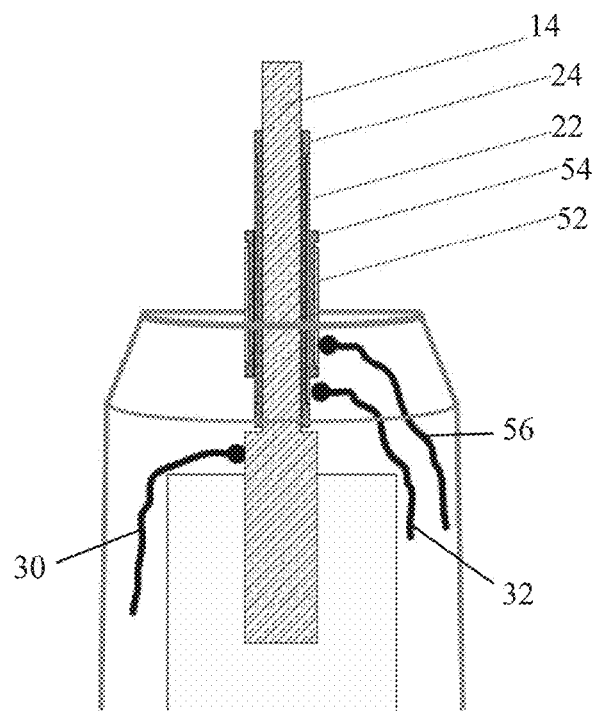
FIG. 8 is an enlarged illustration of a shaft that extends from the vibrator to the brush head in the personal hygiene device of FIG. 5, showing RF electrical connections.

As seen best in FIG. 2, shaft 14 may include an outer conductive sleeve 22 which is electrically insulated from an inner portion of shaft 14 by an insulative sleeve 24. The sleeves are preferably, but not necessarily, concentric with shaft 14.

Shaft 14 includes electrical contacts for transferring electrical energy from an electrical source 26 to electrical elements 28 located in brush head 16. Non-limiting examples of electrical elements include electrodes, RF electrodes (as in the illustrated embodiment), lasers, such as laser diodes, sensors, indicators, lights (e.g., LEDs) or other electrical components. The sensor may be a sensor that senses if the brush head 16 makes contact with hair or skin, such as a capacitance sensor, or an optical sensor for sensing skin or hair color, or a temperature sensor for sensing skin or hair temperature, or any other suitable sensor. The electrodes, RF electrodes or lasers may be used for ablation, skin care, depilation and the like.

The electrical source 26 located in hand piece 13 may be a battery (e.g., rechargeable battery). A battery charger may be provided in hand piece 13 for recharging the battery.

Additionally or alternatively, as in the illustrated embodiment, the electrical source 26 may be an RF generator which is powered by a voltage source (battery), for generating RF energy in a frequency range, typically but not limited to, 500 KHz-30 MHz. The electrodes may operate in monopolar, bipolar or combined monopolar and bipolar modes. Alternatively or additionally, the electrical source 26 may be a microcurrent source for generating galvanic energy in a current range, typically but not limited to 50 microamperes to 250 microamperes. The current may be DC or may be in a frequency range of, typically but not limited to, 1 Hz-500 Hz.

In the illustrated embodiment, the RF generator 26 is connected to the central portion of shaft 14 by a first RF connector 30 and to conductive sleeve 22 with a second RF connector 32. (The first and second RF connectors are also referred to as proximal electrical contacts.) As seen best in FIG. 2, shaft 14 may be formed with a counterbore 20 in which a first brush head RF connector 18 is inserted and in electrical communication with shaft 14. A second brush head RF connector 34 contacts conductive sleeve 22. The first and second brush head RF connectors 18 and 34 (also referred to as distal electrical contacts) are in electrical contact with RF electrodes 28 via conductors 31. This completes the electrical connection from the RF generator to the RF electrodes. As mentioned above, the RF electrodes may be bipolar (both active electrodes) or may be monopolar (one active and the other dispersive, or used with a dispersive electrode external to the device) or a combination thereof. The RF electrodes may be separated by an insulative barrier 40 located among the bristles 19.

Reference is now made to FIGS. 5-8, which illustrate a personal hygiene device 50, constructed and operative in accordance with another non-limiting embodiment of the present invention. Personal hygiene device 50 is similar to personal hygiene device 10, and like elements are designated by like numerals.

Personal hygiene device 50 differs from personal hygiene device 10 in that one of the RF electrical connections serves as a sensing circuit for sensing if the brush head 16 is connected to the hand piece 13, as is now explained.

Personal hygiene device 50 includes an additional outer conductive sleeve 52 which is electrically insulated from conductive sleeve 22 by an additional insulative sleeve 54. The sleeves are preferably, but not necessarily, concentric with shaft 14. A third RF connector 56 is connected to additional conductive sleeve 52.

In the illustrated embodiment, the second brush head RF connector 34 has a first contact point 55 that contacts conductive sleeve 22 and a second contact point 57 that contacts additional outer conductive sleeve 52. If brush head 16 is connected to hand piece 13, the contact points 55 and 57 of second brush head RF connector 34 create a short circuit between conductive sleeve 22 and additional conductive sleeve 52. The control circuitry of the device 50 senses this short circuit and registers that the brush head is properly installed on the hand piece. An indicator may be provided (e.g., an indicator light or audible sound) that the brush head is properly installed on the hand piece. Conversely, if brush head 16 is not connected to hand piece 13, the contact points 55 and 57 of second brush head RF connector 34 do not create a short circuit between conductive sleeve 22 and additional conductive sleeve 52. The control circuitry of the device 50 senses this and registers that the brush head is not properly installed on the hand piece, again with an optional indication to the user.

What is claimed is:

1. A personal hygiene device comprising:
    a vibrator housed in a handle; and
    a shaft coupled to said vibrator that extends from said vibrator to a brush head, said shaft being electrically conducting and comprising one or more proximal electrical contacts in electrical contact with an electrical source and one or more distal electrical contacts in electrical contact with one or more electrical elements located in said brush head, and wherein said shaft is configured to transfer vibrational energy created by said vibrator to said brush head to vibrate said brush head, and wherein said shaft comprises a first conductive sleeve electrically insulated from an inner portion of said shaft by an insulative sleeve.

2. The personal hygiene device according to claim 1, wherein said shaft is rigid.

3. The personal hygiene device according to claim 1, wherein said shaft is flexible.

4. The personal hygiene device according to claim 1, wherein said one or more electrical elements comprise one or more electrodes.

5. The personal hygiene device according to claim 1, wherein said one or more electrical elements comprise one or more RF electrodes.

6. The personal hygiene device according to claim 1, wherein said shaft transfers vibrational energy to said brush head in one-to-one correspondence with vibrations created by said vibrator.

7. The personal hygiene device according to claim 1, wherein said shaft modifies vibrational energy created by said vibrator.

8. The personal hygiene device according to claim 1, comprising an additional outer conductive sleeve which is electrically insulated from said first conductive sleeve by an additional insulative sleeve.

9. The personal hygiene device according to claim 1, wherein said shaft is assembled to said brush head with a snug fit.

10. The personal hygiene device according to claim 1, wherein said shaft is assembled to said brush head with a snap fit.

* * * * *